（12） United States Patent
Eom et al.

(10) Patent No.: US 11,150,183 B2
(45) Date of Patent: Oct. 19, 2021

(54) OPTICAL SENSOR INCLUDING A BASE SUBSTRATE WITH A CONTACT SENSOR AND APPARATUS AND METHOD FOR ESTIMATING BIO-INFORMATION

(71) Applicant: SAMSUNG ELECTRONICS CO., LTD., Suwon-si (KR)

(72) Inventors: Kun Sun Eom, Yongin-si (KR); Jin Young Park, Hwaseong-si (KR); Sung Mo Ahn, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 210 days.

(21) Appl. No.: 16/661,277

(22) Filed: Oct. 23, 2019

(65) Prior Publication Data
US 2020/0124529 A1 Apr. 23, 2020

(30) Foreign Application Priority Data
Oct. 23, 2018 (KR) ........................ 10-2018-0126621

(51) Int. Cl.
*A61B 5/024* (2006.01)
*G01N 21/49* (2006.01)
*G01S 17/88* (2006.01)
*G01N 21/59* (2006.01)

(52) U.S. Cl.
CPC ......... *G01N 21/49* (2013.01); *A61B 5/02427* (2013.01); *G01S 17/88* (2013.01); *G01N 2021/5957* (2013.01)

(58) Field of Classification Search
CPC . A61B 5/14532; A61B 5/157; A61B 5/02427; A61B 5/0059; B01L 2300/0636; G01N 21/49; G01N 2021/3181; G01N 21/314
USPC ........................ 250/559.1, 214 R, 221, 214.1
See application file for complete search history.

(56) References Cited

U.S. PATENT DOCUMENTS

| 7,613,486 | B2 | 11/2009 | Yeo et al. | |
| 8,912,480 | B2 * | 12/2014 | Pope ..................... | G01J 1/0488 250/221 |
| 2007/0021672 | A1 | 1/2007 | Lee et al. | |
| 2016/0166162 | A1 | 6/2016 | Yamaji et al. | |
| 2016/0334332 | A1 | 11/2016 | Magnussen et al. | |

FOREIGN PATENT DOCUMENTS

| JP | 2001-000422 A | 1/2001 |
| JP | 2007-330638 A | 12/2007 |
| JP | 2008-48987 A | 3/2008 |
| JP | 2009-201894 A | 9/2009 |
| JP | 2009-201918 A | 9/2009 |
| JP | 2011-92452 A | 5/2011 |
| KR | 10-0471645 B1 | 3/2005 |

* cited by examiner

*Primary Examiner* — Que Tan Le
(74) *Attorney, Agent, or Firm* — Sughrue Mion, PLLC

(57) ABSTRACT

An optical sensor includes at least one pair of a light source and a photodetector, the light source and the photodetector facing each other and having an opening between the light source and the photodetector; and a base substrate disposed on or below the at least one pair of the light source and the photodetector, the base substrate including a contact sensor positioned in an area corresponding to the opening.

18 Claims, 10 Drawing Sheets

OPTICAL SENSOR INCLUDING A BASE SUBSTRATE WITH A CONTACT SENSOR AND APPARATUS AND METHOD FOR ESTIMATING BIO-INFORMATION

CROSS-REFERENCE TO RELATED APPLICATION(S)

This application claims priority to Korean Patent Application No. 10-2018-0126621, filed on Oct. 23, 2018, in the Korean Intellectual Property Office, the entire disclosure of which is incorporated by reference herein for all purposes.

BACKGROUND

1. Field

Example embodiments of the present disclosure relate to a technology for non-invasively estimating bio-information.

2. Description of Related Art

Healthcare technology has attracted much attention due to the rapid entry into an aging society and relevant social problems such as increase in medical expenses. Accordingly, not only medical devices that can be utilized by hospitals and inspection agencies but also small-sized medical devices that can be carried by individuals, such as wearable devices, are being developed.

Active oxygen is an important biological protective factor and is used for, for example, the bactericidal action of leukocytes, but excessive production of active oxygen in the body is known to cause various tissue diseases. Common factors for generating active oxygen include stress, alcohol, peroxides, drugs, and the like, and the active oxygen generated by these factors may cause various diseases, such as cerebral diseases, cardiovascular diseases, cancer, digestive tract diseases, liver diseases, arteriosclerosis, aging, and the like. The living body has a series of oxidation protection systems to protect itself from oxygen toxicity. It is important to consume enough antioxidant ingredients to properly operate these systems. Antioxidants include vitamin E, vitamin C, carotenoids, and flavonoids. For antioxidant activity, foods containing these antioxidants should be consumed as much as possible.

Thus, research has been conducted on small-sized devices that allow for checking of the amount of antioxidant components in the body.

SUMMARY

Example embodiments provide an optical sensor, and an apparatus and a method for estimating bio-information.

According to an aspect of an example embodiment, there is provided an optical sensor includes at least one pair of a light source and a photodetector, the light source and the photodetector facing each other at a predetermined distance and having an opening between the light source and the photodetector; and a base substrate disposed on or below the at least one pair of the light source and the photodetector, the base substrate including a contact sensor positioned in an area corresponding to the opening.

The base substrate may further include a pressure sensor configured to obtain a contact pressure between the base substrate and an object placed in the opening and contacting the base substrate.

The base substrate may further include an upwardly protruding curved surface in the area corresponding to the opening.

The light source and the photodetector may be mounted on a printed circuit board (PCB) or a flexible printed circuit board (FPCB).

The light source may be configured to emit light of a predetermined wavelength to an object placed in the opening, and the photodetector may be configured to obtain an optical signal based on the light emitted by the light source and passed through the object.

The light source may be configured to emit light of a visible wavelength including a blue wavelength.

According to an aspect of another example embodiment, there is provided an apparatus for estimating bio-information, including: at least one pair of a light source and a photodetector, the light source and the photodetector facing each other and having an opening between the light source and the photodetector; a base substrate disposed on or below the at least one pair of the light source and the photodetector, the base substrate including a contact sensor positioned in an area corresponding to the opening; and a processor configured to obtain an optical signal of an object, placed in the opening and contacting the base substrate, based on operations of the light source and the photodetector, and configured to estimate bio-information of the object based on the obtained optical signal.

The base substrate may further include an upwardly protruding curved surface in the area corresponding to the opening.

The light source may be configured to emit light of a predetermined wavelength to the object and the photodetector is configured to obtain the optical signal based on the light emitted by the light source and passed through the object.

The light source may be configured to emit light of a visible wavelength including a blue wavelength.

The base substrate may further include a contact sensor configured to obtain a contact pressure between the object and the base substrate, and the processor may be configured to provide to the user, based on the contact pressure being smaller than a predetermined threshold pressure, information indicating to increase the contact pressure.

The processor may be configured to determine absorbance of a first wavelength based on the obtained optical signal and estimate the bio-information of the object based on the determined absorbance of the first wavelength.

The first wavelength may be a blue wavelength.

The processor may be configured to determine absorbance of a first wavelength and absorbance of a second wavelength based on the obtained optical signal, configured to preprocess the determined absorbance of the first wavelength based on the determined absorbance of the second wavelength, and configured to estimate the bio-information of the object based on the preprocessed absorbance of the first wavelength.

The first wavelength may be a blue wavelength and the second wavelength may be at least one of a red wavelength or a green wavelength.

The processor may be configured to preprocess the absorbance of the first wavelength by subtracting the absorbance of the second wavelength from the absorbance of the first wavelength or by dividing the absorbance of the first wavelength by the absorbance of the second wavelength.

The bio-information may include information relating to an antioxidant level.

According to an aspect of another example embodiment, there is provided a method of estimating bio-information using an optical sensor, the optical sensor including at least one pair of a light source and a photodetector and a base substrate disposed on or below the at least one pair of the light source and the photodetector, the light source and the photodetector facing each other and having an opening between the light source and the photodetector, the base substrate including a contact sensor positioned in an area corresponding to the opening, the method including: obtaining an optical signal of an object based on operations of the light source and the photodetector, the object placed in the opening and contacting the base substrate; and estimating bio-information of the object based on the obtained optical signal.

BRIEF DESCRIPTION OF THE DRAWINGS

The above and/or other aspects will become apparent and more readily appreciated from the following description of example embodiments, taken in conjunction with the accompanying drawing, in which.

DETAILED DESCRIPTION

Figure 1:
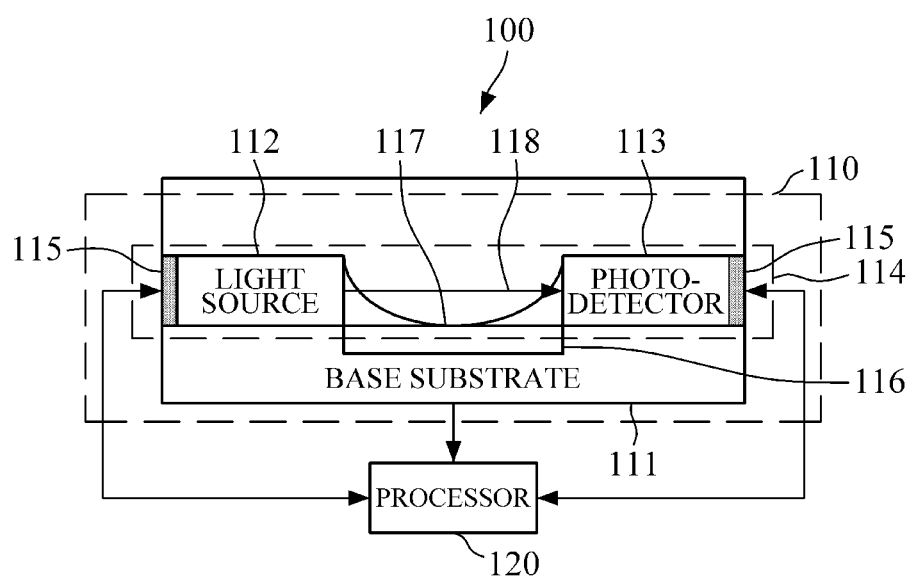
FIG. 1 is a diagram illustrating an apparatus for estimating bio-information according to an example embodiment.

The following detailed description is provided to assist the reader in gaining a comprehensive understanding of the methods, apparatuses and/or systems described herein. Various changes, modifications, and equivalents of the systems, apparatuses and/or methods described herein will suggest themselves to those of ordinary skill in the art. In the following description, a detailed description of known functions and configurations incorporated herein will be omitted when it may obscure the subject matter with unnecessary detail.

Throughout the drawings and the detailed description, unless otherwise described, the same drawing reference numerals will be understood to refer to the same elements, features, and structures. The relative size and depiction of these elements may be exaggerated for clarity, illustration, and convenience.

It should be noted that in some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

Terms described in below are selected by considering functions in the embodiment and meanings may vary depending on, for example, a user or operator's intentions or customs. Therefore, in the following embodiments, when terms are specifically defined, the meanings of terms should be interpreted based on definitions, and otherwise, should be interpreted based on general meanings recognized by those skilled in the art.

It will be understood that, although the terms "first," "second," etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising" will be understood to imply the inclusion of stated elements but not the exclusion of any other elements. Terms such as "unit" and "module" denote units that process at least one function or operation, and they may be implemented by using hardware, software, or a combination of hardware and software.

As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

FIG. 1 is a diagram illustrating an apparatus for estimating bio-information according to an example embodiment.

An apparatus 100 for estimating bio-information as shown in FIG. 1 is an apparatus capable of non-invasively estimating bio-information of an object and may be mounted in an electronic device, or be configured as a separate apparatus enclosed by a housing. The electronic device may include a mobile phone, a smartphone, a tablet computer, a notebook computer, a personal digital assistant (PDA), a portable multimedia player (PMP), a navigation system, an MP3 player, a digital camera, a wearable device, and the like, and the wearable device may include a wrist watch type, a wrist band type, a ring type, a belt type, a necklace type, an ankle band type, a thigh band type, a forearm band type, and the like. However, the electronic device and the wearable device according to the disclosure is not limited to in the above examples.

Referring to FIG. 1, the apparatus 100 for estimating bio-information may include an optical sensor 110 and a processor 120. The processor 120 may be configured by one or more processors, a memory, or a combination thereof.

The optical sensor 110 may include a base substrate 111 and one or more light source-photodetector pairs 114 (or one or more pairs of a light source and a photodetector), each including a light source 112 and a photodetector 113.

The base substrate 111 below the one or more light source-photodetector pairs 114 may support one or more light source-photodetector pairs 114. A contact sensor 116 may be disposed on the base substrate 111 in an area below an aperture (or opening) formed between the light source 114 and the photodetector 113. The contact sensor 116 may detect whether the object 117 inserted (or placed) in the aperture is in contact with the base substrate 111.

The base substrate 111 may further include a pressure sensor configured to measure a contact pressure between the base subtracted 111 and the object placed in the aperture.

The light source 112 and the photodetector 113 of the light source-photodetector pair 114 may be disposed on the base substrate 111 such that they face each other at a predetermined distance. The light source 112 and the photodetector 113 may each be mounted on a printed circuit board (PCB) or a flexible printed circuit board (FPCB) 115. The aperture may be formed between the light source 112 and the photodetector 113 and may act as a sort of a channel, and the object may be placed in the aperture.

The light source 112 may emit light 118 of a predetermined wavelength to the object placed in the aperture in response to a predetermined control signal. According to an example embodiment, the light source 112 may emit light of a visible wavelength including a blue wavelength. However, the wavelength of light emitted from the light source 112 may vary depending on the purpose of measurement or the type of a component to be analyzed. In addition, the light source may not be necessarily formed as a single light emitter and may be formed as a group of a plurality of light emitters. According to an example embodiment, the light source 112 may include a light emitting diode (LED), a laser diode, and a phosphor, but these are merely examples, and the light source 511 is not limited thereto.

In a case in which the optical sensor 110 includes a plurality of light sources, the plurality of light sources may emit light of the same wavelength or emit light of different wavelengths. In addition, some of the plurality of light sources may emit light of the same wavelength and other light sources may emit light of different wavelengths.

The photodetector 113 may measure an optical signal by receiving light passing through the object placed in the aperture. According to an example embodiment, the photodetector 113 may be formed by a photodiode, a phototransistor, or a charge coupled device (CCD), but embodiments are not limited thereto.

The processor 120 may control an overall operation of the apparatus 100 for estimating bio-information.

The processor 120 may obtain an optical signal by driving the light source 112 when the object is placed in the aperture and brought into contact with the base substrate 111.

The processor 120 may estimate the bio-information of the object by analyzing the obtained optical signal. In an example embodiment, the bio-information may be an anti-oxidant level.

According to an example embodiment, the processor 120 may determine absorbance of a first wavelength based on the obtained optical signal and estimate bio-information of the object using the absorbance of the first wavelength and a first bio-information estimation model. In this case, the first wavelength may be a blue wavelength. The first bio-information estimation model may define a relationship between the absorbance of the first wavelength and the bio-information, may be established through regression analysis or machine learning, and may be stored in an internal or external memory of the processor 120. The first bio-information estimation model may be established in the form of a mathematical algorithm or a matching table, but is not limited thereto.

According to an example embodiment, the processor 120 may determine absorbance of the first wavelength and absorbance of a second wavelength based on the optical signal and preprocess the absorbance of the first wavelength on the absorbance of the second wavelength. In this case, the first wavelength may be a blue wavelength and the second wavelength may be at least one of a green wavelength or a red wavelength. For example, the processor 120 may preprocess the absorbance of the first wavelength by subtracting the absorbance of the second wavelength from the absorbance of the first wavelength or dividing the absorbance of the first wavelength by the absorbance of the second wavelength, thereby removing influences from substances other than a bio-information target substance (e.g., an antioxidant substance (carotenoid or the like)). However, the disclosure is not limited thereto, and the processor 120 may preprocess the absorbance of the first wavelength in any other manner so as to remove or reduce influences from substances other than the bio-information target substance.

The processor 120 may estimate bio-information of the object using the preprocessed absorbance of the first wavelength and a second bio-information estimation model. The second bio-information estimation model may define a relationship between the preprocessed absorbance of the first wavelength and the bio-information. The second bio-information estimation model may be established through regression analysis or machine learning, and may be stored in an internal or external memory. The second bio-information estimation model may be in the form of a mathematical algorithm or a matching table, but is not limited thereto.

The processor 120 may guide a user's action so that the contact pressure between the base substrate 111 and the object becomes greater than or equal to a predetermined threshold pressure. For example, when the contact pressure between the base substrate 111 and the object is smaller than the predetermined threshold pressure or when the contact pressure, although greater than or equal to the predetermined threshold pressure, is not maintained for a predetermined period of time, the processor 120 may determine that the contact pressure sufficient to obtain the optical signal to be used in estimating bio-information is not applied, generate guide information for guiding a user's action to increase the contact pressure between the base substrate 111 and the object, and provide the guide information to the user through an output device or interface (e.g., output hardware or output circuitry). The output device or interface may include a visual output device or interface (e.g., a display or the like), an audible output device or interface (e.g., a speaker or the like), a tactile output device or interface (e.g., a vibrator or the like), and the like. In addition, when the contact pressure between the base substrate 111 and the object is greater than or equal to the predetermined threshold pressure or when the contact pressure is maintained to be greater than or equal to the predetermined threshold pressure for a predetermined period of time, the processor 120 may determine that a contact pressure sufficient to obtain an optical signal in estimating the bio-information is applied, and obtain the optical signal by driving the light source 112.

When the estimated bio-information deviates from a predetermined baseline, the processor 120 may generate an advisory message and provide the advisory message to the user through the above-described output device or interface so that the bio-information does not deviate from the predetermined baseline. For example, when the bio-information is not an antioxidant level and an estimated antioxidant level is below a predetermined threshold level, the processor 120 may generate the advisory message, such as "please eat more vegetables," "please smoke less," "please drink less alcohol," "please do more exercise," "please reduce your stress," or the like, to increase the antioxidant level, and may provide the advisory message to the user through the output device or interface.

The apparatus 100 for estimating bio-information may further include a cover above the light source-photodetector pair 114 to protect the light source-photodetector pair 114.

Figure 2:
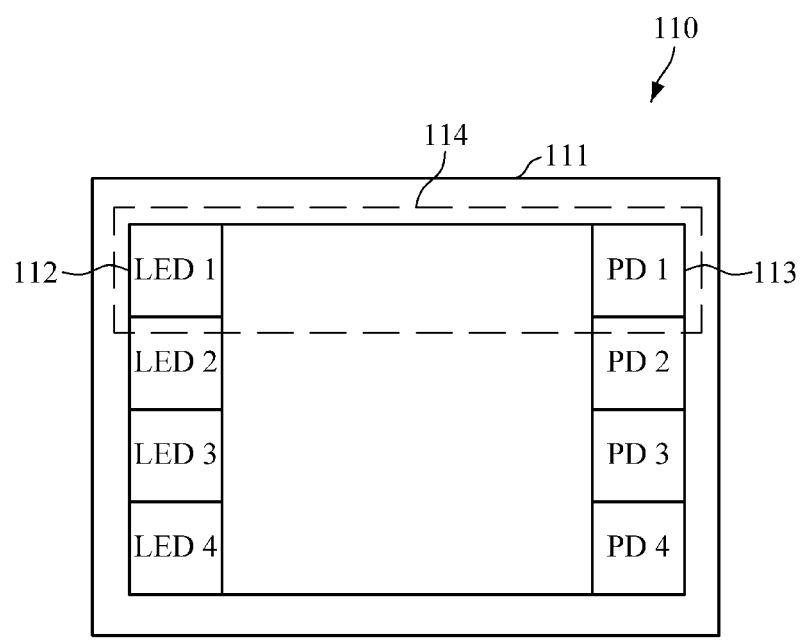
FIG. 2 is a diagram illustrating an arrangement of light source-photodetector pairs according to an example embodiment.
Figure 3:
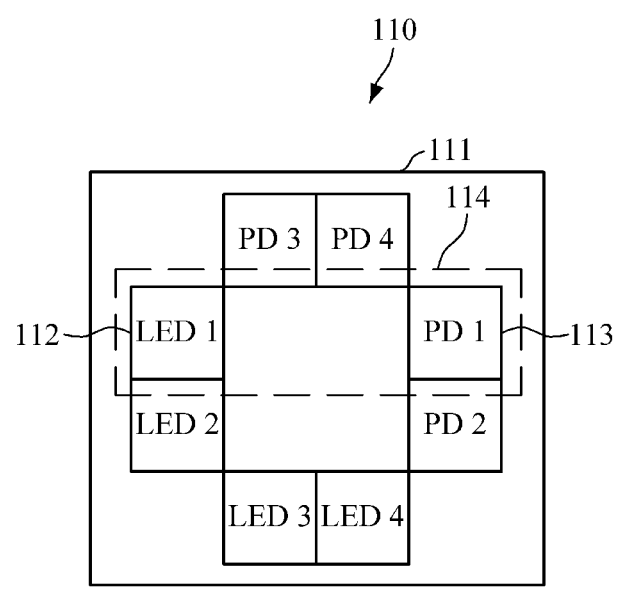
FIG. 3 is a diagram illustrating an arrangement of light source-photodetector pairs according to an example embodiment.
Figure 4:
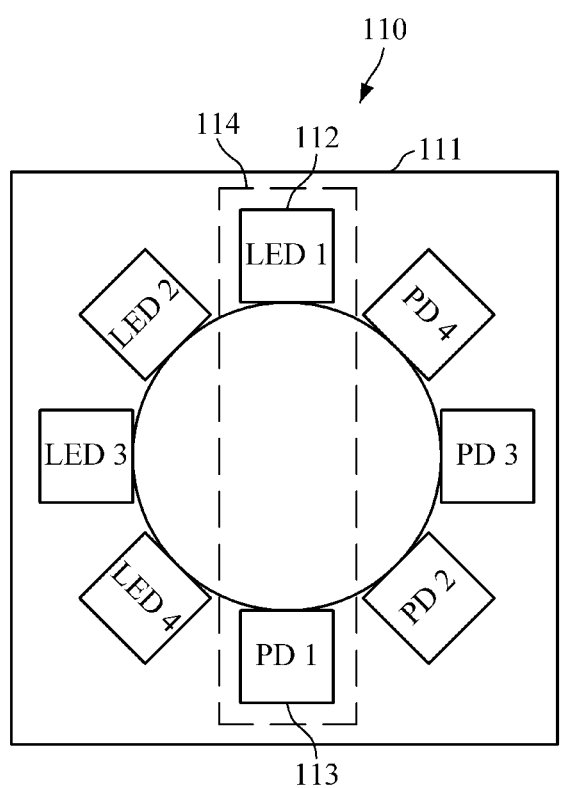
FIG. 4 is a diagram illustrating an arrangement of light source-photodetector pairs according to an example embodiment.

FIGS. 2, 3, and 4 are diagrams illustrating an arrangement of light source-photodetector pairs according to example embodiments. FIGS. 2, 3, and 4 illustrate four light source-photodetector pairs, but this is merely an example, and the number of light source-photodetector pairs is not limited.

Referring to FIGS. 2, 3, and 4, the optical sensor 110 may include a base substrate 111 and a plurality of light source-photodetector pairs 114 on the base substrate 111, wherein each of the light source-photodetector pairs 114 includes a light source 112 and a photodetector 113 that face each other at a predetermined distance. As shown in FIG. 2, a plurality of light sources 112 positioned in a straight array and a plurality of photodetectors 113 positioned in a straight array may be disposed to face each other, or as shown in FIG. 3, a plurality of light sources 112 positioned in an "L"-shaped array and a plurality of photodetectors 113 positioned in a "¬"-shaped array may be disposed to face each other. Alternatively, as show in FIG. 4, a plurality of light sources 112 positioned in a semicircular array and a plurality of photodetectors 113 positioned in a semicircular array may be disposed to face each other. However, the arrangements shown in FIGS. 2 to 4 are merely examples and the arrangement of the light sources and the photodetectors is not limited thereto.

Figure 5:
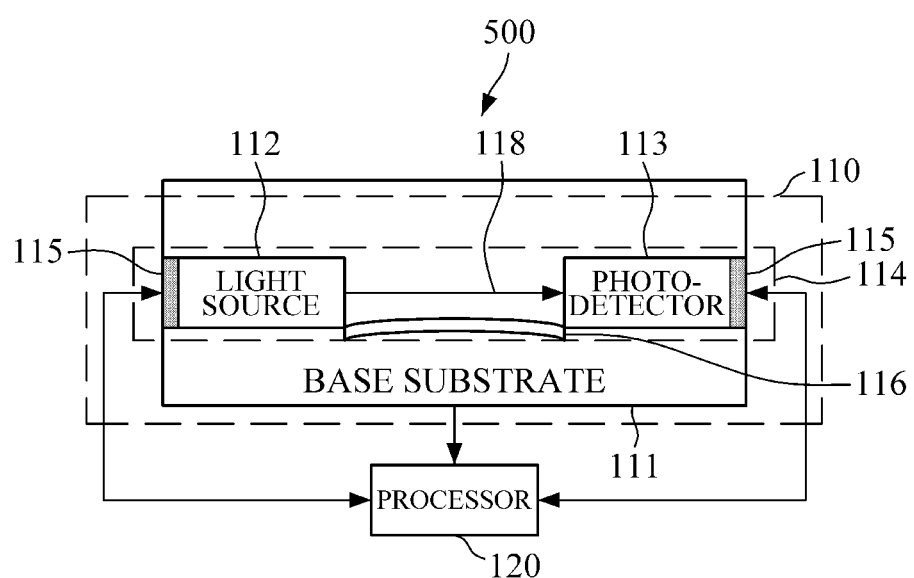
FIG. 5 is a diagram illustrating an apparatus for estimating bio-information according to an example embodiment.

FIG. 5 is a diagram illustrating an apparatus for estimating bio-information according to an example embodiment.

An apparatus 500 for estimating bio-information as shown in FIG. 5 may be a modification of the apparatus 100 of FIG. 1 in which the shape of the base substrate 111 is changed. As shown in FIG. 5, a base substrate 111 of the apparatus 500 for estimating bio-information may have an upwardly protruding curved portion below an aperture (or opening) in which a contact sensor 116 is installed. Based on this configuration, an object can be easily in contact with the base substrate 111 and easily apply a contact pressure between the base substrate 111 and the object with a small amount of force.

Figure 6:
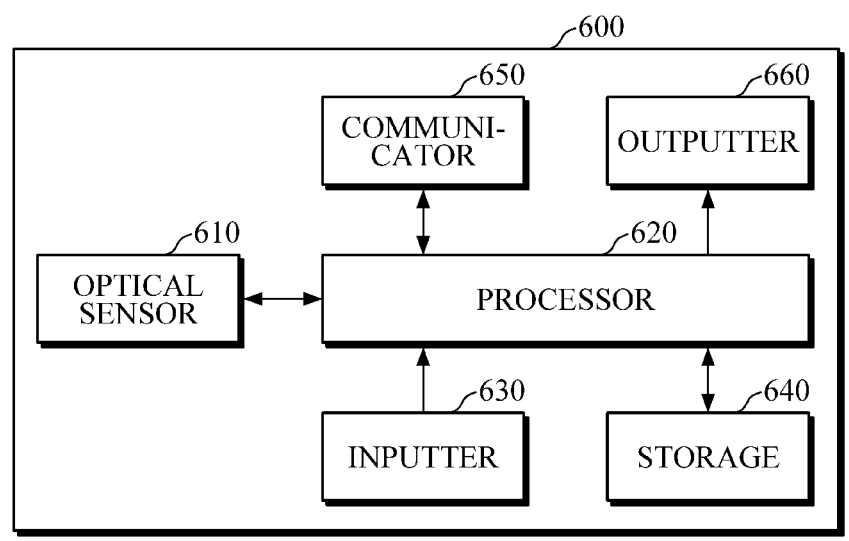
FIG. 6 is a diagram illustrating an apparatus for estimating bio-information according to an example embodiment.

FIG. 6 is a diagram illustrating an apparatus for estimating bio-information according to an example embodiment.

An apparatus 600 for estimating bio-information as shown in FIG. 6 may be an apparatus capable of non-invasively estimating bio-information of an object and may be mounted in an electronic device or be configured as a separate apparatus enclosed by a housing. The electronic device may include a mobile phone, a smartphone, a tablet computer, a notebook computer, a PDA, a PMP, a navigation system, an MP3 player, a digital camera, a wearable device, and the like, and the wearable device may include a wrist watch type, a wrist band type, a ring type, a belt type, a necklace type, an ankle band type, a thigh band type, a forearm band type, and the like. However, the electronic device and the wearable device may not be included in the above examples.

Referring to FIG. 6, the apparatus 600 for estimating bio-information may include an optical sensor 610, a processor 620, an inputter (or input interface) 630, a storage 640, a communicator (or communication interface) 650, and an outputter (or output interface) 660. In this case, the optical sensor 610 and the processor 620 are substantially the same as or similar to the optical sensor 110 and the processor 102 which are described with reference to FIGS. 1 to 5, and thus detailed descriptions thereof will not be reiterated.

The inputter 630 may receive various operation signals from a user. According to an example embodiment, the inputter 630 may include a key pad, a dome switch, a touch pad, a jog wheel, a jog switch, a hardware button, and the like. In particular, when a touch pad has a layered structure with a display, this structure may be referred to as a touch screen.

A program or commands for operations of the apparatus 600 for estimating bio-information may be stored in the storage 640 and data input to and output from the apparatus 600 may be stored in the storage 640. In addition, the data processed by the apparatus 600 for estimating bio-information, data (e.g., a bio-information estimation model and the like) to be used for data processing of the apparatus 600, and the like may be stored in the storage 640.

The storage 640 may include at least one type of storage medium, such as a flash memory type, a hard disk type, a multimedia card micro type, a card type memory (e.g., SD or XD memory) random access memory (RAM), static random access memory (SRAM), read-only memory (ROM), electrically erasable programmable read-only memory (EEPROM), programmable read-only memory (PROM), a magnetic memory, a magnetic disk, and an optical disk. In addition, the apparatus 600 for estimating bio-information may operate on an external storage medium, such as a web storage that performs the storage function of the storage 640 on the Internet.

The communicator 650 may communicate with an external device. For example, the communicator 650 may transmit data handled by the apparatus 600 for estimating bio-information or processing result data of the apparatus 600 for estimating bio-information to the external device or receive a variety of data useful to measure an optical signal and/or estimate bio-information from the external device.

In this case, the external device may be a medical device which uses the data handled by the apparatus 600 or processing result data of the apparatus 600, or a printer or a display device for outputting a result. In addition, the external device may include a digital TV, a desktop computer, a mobile phone, a smartphone, a tablet computer, a notebook computer, a PDA, a PMP, a navigation system, an MP3 player, a digital camera, a wearable device, and the like, but is not limited thereto.

The communicator 650 may be a communication interface that communicates with the external device using Bluetooth communication, Bluetooth low energy (BLE) communication, near field communication (NFC), wireless local access network (WLAN) communication, ZigBee communication, infrared data association (IrDA) communication, Wi-Fi direct (WFD) communication, ultra-wideband (UWB) communication, Ant+ communication, Wi-Fi communication, radio frequency identification (RFID) communication, 3G communication, 4G communication, and 5G communication. However, these are merely examples and the types of communication and embodiments are not limited thereto.

The outputter 660 may output the data handled by the apparatus 600 for estimating bio-information or the processing result data of the apparatus 600. According to an example embodiment, the outputter 660 may output the data handled by the apparatus 600 for estimating bio-information or the processing result data of the apparatus 600 using at least one of an audible method, a visual method, and a tactile method. To this end, the outputter 660 may include a display, a speaker, a vibrator, and the like.

Figure 7:
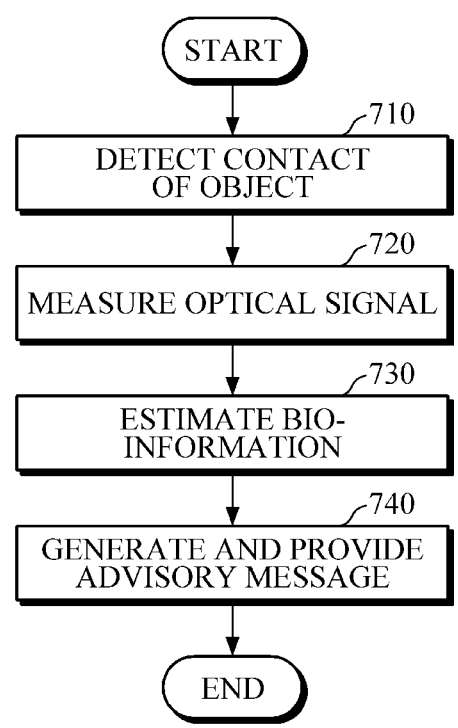
FIG. 7 is a flowchart illustrating a method of estimating bio-information according to an example embodiment.

FIG. 7 is a flowchart illustrating a method of estimating bio-information according to an example embodiment. The method of FIG. 7 to estimate bio-information may be performed by any one of the apparatuses 100, 500, and 600 of FIGS. 1, 5, and 6.

Referring to FIG. 7, the apparatus for estimating bio-information may detect whether an object placed in an aperture (or opening) formed between a light source and a photodetector is in contact with a base substrate (710).

The apparatus for estimating bio-information may measure an optical signal by driving the light source when the object is placed in the aperture and is in contact with the base substrate (720).

The apparatus for estimating bio-information may estimate bio-information of the object by analyzing the measured optical signal (730). In an example embodiment, the bio-information may be an antioxidant level.

When the estimated bio-information deviates from a predetermined baseline, the apparatus for estimating bio-information may generate an advisory message and provide the advisory message to a user through an output device or interface so that the bio-information does not deviate from the predetermined baseline (740). For example, when the bio-information is an antioxidant level and an estimated antioxidant level is below a predetermined threshold level, the apparatus for estimating bio-information may generate the advisory message, such as "please eat more vegetables," "please smoke less," "please drink less alcohol," "please do more exercise," "please reduce your stress," or the like, to increase the antioxidant level, and may provide the advisory message to the user through the output device or interface.

Figure 8:
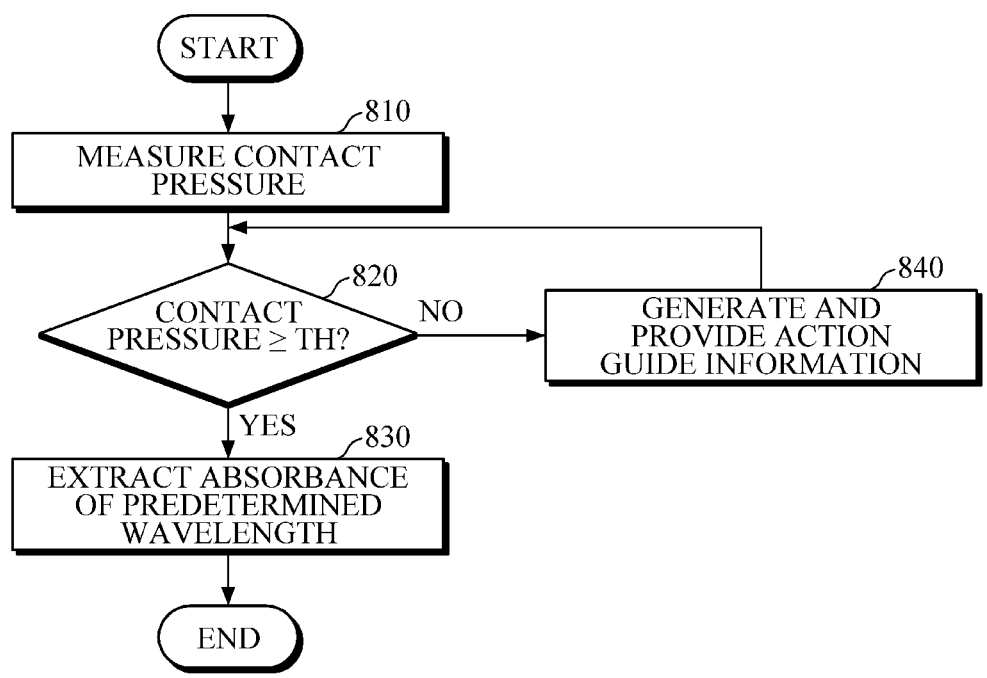
FIG. 8 is a flowchart illustrating a method of obtaining an optical signal according to an example embodiment.

FIG. 8 is a flowchart illustrating a method of obtaining an optical signal according to an example embodiment. The method of FIG. 8 may be an example embodiment of operation 720 of FIG. 7 to measure an optical signal.

Referring to FIG. 8, the apparatus for estimating bio-information may measure a contact pressure between a base substrate and an object (810) and compare the measured contact pressure with a predetermined threshold pressure (TH) (820).

When the contact pressure is greater than or equal to the predetermined threshold pressure (TH), the apparatus for estimating bio-information may determine that the contact pressure sufficient to measure an optical signal to be used in estimating bio-information is applied and may measure an optical signal by driving a light source (830).

When the contact pressure is smaller than the predetermined threshold pressure (TH), the apparatus for estimating bio-information may determine that a contact pressure sufficient to measure an optical signal to be used in estimating bio-information is not applied, and generate action guide information for the user to increase the contact pressure between the base substrate and the object and provide the action guide information to the user through an output device or interface (840).

The apparatus for estimating bio-information may further take into account a duration time, as well as the magnitude of the contact pressure. For example, when the contact pressure is maintained to be greater than or equal to the predetermined threshold pressure (TH), the apparatus may measure an optical signal and when the contact pressure is smaller than the predetermined threshold pressure (TH) or when the contact pressure, although greater than or equal to the predetermined threshold pressure, is not maintained for a predetermined period of time, the apparatus may generate action guide information and provide the action guide information to the user through the output device or interface.

Figure 9:
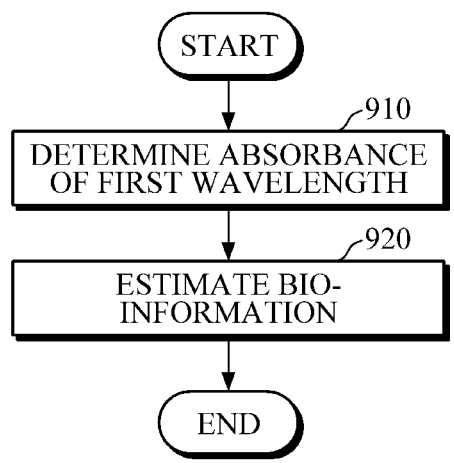
FIG. 9 is a flowchart illustrating a method of estimating bio-information of an object by analyzing an optical signal according to an example embodiment.

FIG. 9 is a flowchart illustrating a method of estimating bio-information of an object by analyzing an optical signal according to an example embodiment. The method of FIG. 9 may be an example embodiment of operation 730 of FIG. 7 to estimate bio-information.

Referring to FIG. 9, the apparatus for estimating bio-information may determine absorbance of a first wavelength based on a measured optical signal (910). In an example embodiment, the first wavelength may be a blue wavelength.

The apparatus for estimating bio-information may estimate bio-information of an object using absorbance of the first wavelength and a first bio-information estimation model (920). The first bio-information estimation model defines a relationship between the absorbance of the first wavelength and the bio-information and may be established in advance through regression analysis or machine learning. The first bio-information estimation model may be established in the form of a mathematical algorithm or a matching table, but is not limited thereto.

Figure 10:
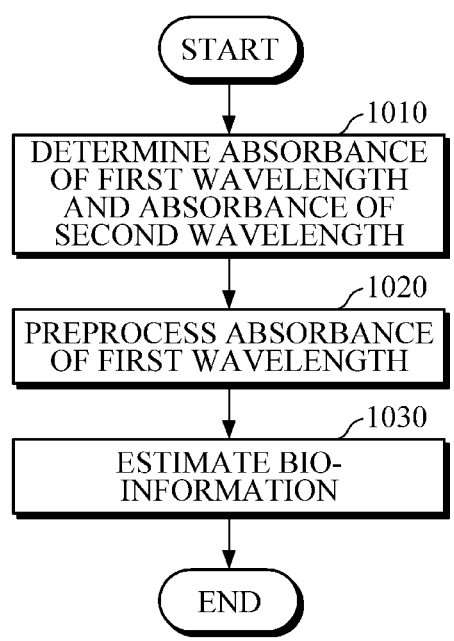
FIG. 10 is a flowchart illustrating a method of estimating bio-information of an object by analyzing an optical signal according to an example embodiment.

FIG. 10 is a flowchart illustrating a method of estimating bio-information of an object by analyzing an optical signal according to an example embodiment. The method of FIG. 10 may be an example embodiment of operation 730 of FIG. 7 to estimate bio-information.

Referring to FIG. 10, the apparatus for estimating bio-information may determine absorbance of a first wavelength and absorbance of a second wavelength based on a measured optical signal (1010). The first wavelength may be a blue wavelength and the second wavelength may be at least one of a green wavelength or a red wavelength.

The apparatus for estimating bio-information may preprocess the absorbance of the first wavelength based on the absorbance of the second wavelength (1020). For example, the apparatus for estimating bio-information may preprocess the absorbance of the first wavelength by subtracting the absorbance of the second wavelength from the absorbance of the first wavelength or dividing the absorbance of the first wavelength by the absorbance of the second wavelength, thereby removing influences from substances other than a bio-information target substance (e.g., an antioxidant substance (carotenoid or the like)).

The apparatus for estimating bio-information may estimate bio-information of the object by using the preprocessed absorbance of the first wavelength and a second bio-information estimation model (920). In this case, the second bio-information estimation model defines a relationship between the preprocessed absorbance of the first wavelength and the bio-information and may be established in advance through regression analysis or machine learning. The second bio-information estimation model may be established in the form of a mathematical algorithm or a matching table, but is not limited thereto.

The current embodiments can be implemented as computer readable codes in a computer readable record medium. Codes and code segments included in the computer program can be easily inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

According to example embodiments, apparatuses and methods capable of obtaining an optical signal to be used for estimating bio-information are provided while reducing the size of (or miniaturizing) the apparatus or a device in which the apparatus is mounted by disposing one or more light source-photodetector pairs to face each other.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing steps may employ any number of related art techniques for electronics configuration, signal processing and/or control, data processing and the like.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

Although example embodiments have been described above, a person of ordinary skill in the art will understand and appreciate that various modifications can be made without departing the scope of the disclosure. Thus, it will be apparent to those ordinary skilled in the art that the true scope of technical protection is only defined by the following claims.

What is claimed is:

1. An optical sensor comprising:
    at least one pair of a light source and a photodetector, the light source and the photodetector facing each other and having an opening between the light source and the photodetector; and
    a base substrate disposed on or below the at least one pair of the light source and the photodetector, the base substrate comprising a contact sensor positioned in an area corresponding to the opening.

2. The optical sensor of claim 1, wherein the base substrate further comprises a pressure sensor configured to obtain a contact pressure between the base substrate and an object placed in the opening and contacting the base substrate.

3. The optical sensor of claim 1, wherein the base substrate further comprises an upwardly protruding curved surface in the area corresponding to the opening.

4. The optical sensor of claim 1, further comprising a printed circuit board or a flexible printed circuit board on which the light source and the photodetector are mounted.

5. The optical sensor of claim 1, wherein the light source is configured to emit light of a predetermined wavelength to an object placed in the opening, and
    wherein the photodetector is configured to obtain an optical signal based on the light emitted by the light source and passed through the object.

6. The optical sensor of claim 5, wherein the light source is configured to emit light of a visible wavelength comprising a blue wavelength.

7. An apparatus for estimating bio-information, the apparatus comprising:
    at least one pair of a light source and a photodetector, the light source and the photodetector facing each other and having an opening between the light source and the photodetector;
    a base substrate disposed on or below the at least one pair of the light source and the photodetector, the base substrate comprising a contact sensor positioned in an area corresponding to the opening; and
    a processor configured to obtain an optical signal of an object, placed in the opening and contacting the base substrate, based on operations of the light source and the photodetector, and to estimate bio-information of the object based on the obtained optical signal.

8. The apparatus of claim 7, wherein the base substrate further comprises an upwardly protruding curved surface in the area corresponding to the opening.

9. The apparatus of claim 7, wherein the light source is configured to emit light of a predetermined wavelength to the object, and
    wherein the photodetector is configured to obtain the optical signal based on the light emitted by the light source and passed through the object.

10. The apparatus of claim 9, wherein the light source is configured to emit light of a visible wavelength comprising a blue wavelength.

11. The apparatus of claim 7, wherein the base substrate further comprises a contact sensor configured to obtain a contact pressure between the object and the base substrate, and
    wherein the processor is further configured to provide to a user, based on the contact pressure being smaller than a predetermined threshold pressure, information indicating to increase the contact pressure.

12. The apparatus of claim 7, wherein the processor is further configured to:
    determine absorbance of a first wavelength based on the obtained optical signal, and
    estimate the bio-information of the object based on the determined absorbance of the first wavelength.

13. The apparatus of claim 12, wherein the first wavelength is a blue wavelength.

14. The apparatus of claim 7, wherein the processor is further configured to:

determine absorbance of a first wavelength and absorbance of a second wavelength based on the obtained optical signal, preprocess the determined absorbance of the first wavelength based on the determined absorbance of the second wavelength, and estimate the bio-information of the object based on the preprocessed absorbance of the first wavelength.

15. The apparatus of claim 14, wherein the first wavelength is a blue wavelength and the second wavelength is at least one of a red wavelength or a green wavelength.

16. The apparatus of claim 14, wherein the processor is further configured to preprocess the absorbance of the first wavelength by subtracting the absorbance of the second wavelength from the absorbance of the first wavelength or by dividing the absorbance of the first wavelength by the absorbance of the second wavelength.

17. The apparatus of claim 7, wherein the bio-information comprises information relating to an antioxidant level.

18. A method of estimating bio-information using an optical sensor, the optical sensor comprising at least one pair of a light source and a photodetector and a base substrate disposed on or below the at least one pair of the light source and the photodetector, the light source and the photodetector facing each other and having an opening between the light source and the photodetector, the base substrate including a contact sensor positioned in an area corresponding to the opening, the method comprising:

obtaining an optical signal of an object based on operations of the light source and the photodetector, the object placed in the opening and contacting the base substrate; and estimating bio-information of the object based on the obtained optical signal.

* * * * *